(12) United States Patent
Cottrell

(10) Patent No.: US 8,853,282 B1
(45) Date of Patent: Oct. 7, 2014

(54) TOPICAL LIQUID INSECTICIDE COMPOSITIONS

(71) Applicant: Sumitomo Corporation, Tokyo (JP)

(72) Inventor: Ian Cottrell, Spring Hill, FL (US)

(73) Assignee: Sumitomo Corporation, Tokyo (JP)

( * ) Notice: Subject to any disclaimer, the term of this patent is extended or adjusted under 35 U.S.C. 154(b) by 0 days.

(21) Appl. No.: 14/284,658

(22) Filed: May 22, 2014

(51) Int. Cl.
- *A01N 31/14* (2006.01)
- *A61K 31/075* (2006.01)
- *A01N 43/08* (2006.01)
- *A61K 31/34* (2006.01)
- *A01N 33/26* (2006.01)
- *A61K 31/13* (2006.01)
- *C07C 41/00* (2006.01)
- *C07D 307/00* (2006.01)
- *C07C 241/00* (2006.01)
- *A01N 43/40* (2006.01)
- *A01N 47/44* (2006.01)

(52) U.S. Cl.
CPC .............. *A01N 47/44* (2013.01); *A01N 43/40* (2013.01); *A01N 31/14* (2013.01)
USPC ........... 514/721; 514/461; 514/611; 568/636; 549/429; 564/107

(58) Field of Classification Search
None
See application file for complete search history.

(56) References Cited

U.S. PATENT DOCUMENTS

| | | | |
|---|---|---|---|
| 6,867,223 B2 | 3/2005 | Cottrell et al. | |
| 7,345,092 B2 * | 3/2008 | Cottrell et al. | 514/471 |
| 7,354,595 B2 | 4/2008 | Cottrell et al. | |
| 7,368,435 B2 | 5/2008 | Cottrell et al. | |
| 2005/0009880 A1 | 1/2005 | Cottrell et al. | |
| 2005/0009881 A1 | 1/2005 | Cottrell et al. | |
| 2005/0096386 A1 | 5/2005 | Cottrell et al. | |
| 2006/0062817 A1 | 3/2006 | Cottrell et al. | |
| 2006/0211655 A1 | 9/2006 | Mencke et al. | |
| 2007/0078110 A1 | 4/2007 | Nishimoto et al. | |
| 2008/0300313 A1 | 12/2008 | Byrne et al. | |
| 2009/0069387 A1 | 3/2009 | Ecker et al. | |
| 2011/0144166 A1* | 6/2011 | Cottrell et al. | 514/345 |
| 2013/0045996 A1 | 2/2013 | Sirinyan et al. | |
| 2013/0101687 A1 | 4/2013 | Willis et al. | |
| 2013/0231371 A1 | 9/2013 | Nouvel et al. | |

FOREIGN PATENT DOCUMENTS

| | | |
|---|---|---|
| CN | 101874486 | 11/2010 |
| CN | 102239878 A * | 11/2011 |
| CN | 102907454 | 2/2013 |
| JP | 2010111584 A * | 5/2010 |
| WO | WO 2005070210 A1 * | 8/2005 |
| WO | WO 2010/145994 | 12/2010 |

OTHER PUBLICATIONS

Partial Translation of CN102239878A.*
Partial Translation of JP 2010111584A.*

* cited by examiner

*Primary Examiner* — Jeffrey S. Lundgren
*Assistant Examiner* — Michael Schmitt
(74) *Attorney, Agent, or Firm* — Saliwanchik, Lloyd & Eisenschenk

(57) ABSTRACT

A topical liquid formulation is provided which contains a combination of three active ingredients for treating fleas and ticks in domestic animals. Total concentration of the active hydrophobic and hydrophilic ingredients can exceed 60 weight percent. In contrast to commonly available flea treatments, the new insecticidal composition is safe and effective for both felines and canines and a single topical application can be effective for at least several weeks.

20 Claims, No Drawings

TOPICAL LIQUID INSECTICIDE COMPOSITIONS

BACKGROUND OF THE INVENTION

1. Field of the Invention

The invention relates generally to insecticides and more particularly to insecticidal formulations for use on domestic animals such as cats and dogs.

2. Description of Background Art

As dog and cat ownership increases, there has been a proliferation of medical and health services available for addressing the needs of sick and aging pets, as well as the maintenance of young and healthy animals. Veterinarians routinely examine pets for diseases and indications of infections including the presence of parasites or various types of cancers. Cats are particularly prone to feline leukemia and may develop diabetes.

Many diseases affecting the health of both cats and dogs are caused by ticks and fleas that act as vectors for viruses and parasites through bites which can transmit blood borne infections. The market for flea and tick products in the US is approximately $552 million and is dominated by about 9 businesses. Although growth between 2007-2012 was 0.6%, the market is expected to increase over the next five years as there is an increasing number of pet owners, particularly those who consider pets as family members and are willing to spend money for the health and well-being of their pets.

There are several disadvantages in current flea/tick products for dogs and cats. Ideally, in order to address one or more of the deficiencies in currently available flea/tick formulations, a product should have: (1) a high concentration of active ingredient(s) to minimize the volume of a topical needed for application to a small dog or cat; (2) liquid formulations that are stable and effective such that flea kill continues for up to at least 30 days from application; (3) a safe product for the consumer in case of skin contact; (4) a formulation that is stable at ambient, low and higher temperatures with a commercially appropriate shelf life; (5) a product that is nontoxic for a dog or cat if ingested; and (6) a product that is ideally equally safe and effective for use on both dogs and cats.

Many available flea/tick topical compositions are not safe and effective for use in both dogs and cats, the two most common household pets. Another drawback of current products is that higher more effective concentrations of the active ingredients are unavailable in stable liquid form.

An effective topical "spot on" application is a commercially desirable feature, particularly if formulations can be applied based on weight and not species basis of the animal. Some liquid spot products for dogs cannot be used on cats.

U.S. Pat. No. 6,867,223 describes insecticide formulations consisting of pryiproxyfen and up to 25% by weight of dinotefuran dissolved in an alcohol, which is described as applicable for use on both dogs and cats. In U.S. Pat. No. 7,368,435, topical endoparasiticidal and ectoparasiticidal formulations combine a macrocyclic lactone and a neo-nicotinoid in addition to permethrin and an insect growth regulator. The first two components are packaged separately to prevent interaction with the permethrin and cannot be supplied as a stable liquid.

Estimated Feline and Canine Populations

Domestic pets in the United States number in the millions with by far the largest contribution from cats and dogs. The United States cat population in 2012 was estimated at over 74 million cats. The US count does not include feral and community cat populations, which are believed to be approximately 50 million. 30-40 percent of households in the US own one or more cats or dogs. The mean veterinary expenditure per household per year for dogs is $378, comparable to that spent on horses, while for cats the cost average is $191. (2012 U.S. Pet Ownership & Demographics Sourcebook).

Table 1 shows the estimated number of cats and dogs in the top ten countries with the highest populations.

Canine and feline populations are highest in the United States; however, cats are more popular than dogs as pets in the United Kingdom and Germany.

Dogs and cats are a major business in the United States. Growth is continuing in development and expansion of dog and cat food with boutique brands and organic feeds enjoying profitable niche markets. New breeds of dogs and cats are appearing, with so-called designer breeds such as labradoodles and cockapoos and the recognition of additional purebred dogs by such organizations as the American Kennel Club.

Consumers are also becoming more familiar with cat breeds, including ancient breeds, domestic and domestic/wild hybrids. There is inconsistency in breed classification among cat registries. At least 55 different breeds are recognized, but a huge number of cats are mixed breeds. Recognized breeds include natural, crossbreeds, and mutations.

The list of recognized cat breeds is long and includes: Abyssinian, Aegean, Australian Mist, American Curl, American Bobtail, American Polydactyl, American shorthair, American Wirehair, Arabian Man, Asian, Asian Semi-longhair, Balinese, Bambino, Bengal, Birman, Bombay, Brazilian Shorthair, British Shorthair, British Longhair, Burmese, Burmilla, California Spangled Cat, Chantilly/Tiffany, Chartreux, Clausie, Cheetoh, Colorpoint Shorthair, Cornish Rex, Cymric, Cyprus cat, Devon Rex Doinskoy, Dragon Li, Dwelf, Egyptian Mau, European Shorthair, Exotic Shorthair, German Rex, Havana Brown, Highlander, Himalayan/Colorpoint Persian, Japanese Bobtail, Javanese, Khao Manee, Korat, Kurilian Bobtail, LaPerm, Maine Coon, Manx, Mekong bobtail, Minskin, Munchkin, Nebelung, Napoleon, Norwegian Forest Cat, Ocicat, Ojos Azules, Oregon Rex, Oriental Bicolor, Oriental Shorthair, Oriental Longhair, Persian, Peterbald, Pixie-bob, Ragamuffin, Ragdoll, Russian Blue, Russian Black, White or Tabby, Savannah, Scottish Fold, Selkirk Rex, Serengeti cat, Serrade petit, Siamese, Siberian Singapura, Snowshoe, Sokoke, Somali, Sphynx, Swedish forest cat, Thai, Tonkinese, Toyger, Turkish Angora, Turkish Van, Ukrainian Levkoy, and York Chocolate Cat.

The list of American Kennel Club recognized breeds includes Affenpinscher, afghan hound, Airedale Terrier, Akita, Alaskan Malamute, American English Coonhound, American Eskimo Dog, American Foxhound, American Staffordshire Terrier, American Water Spaniel, Anatolian Shepherd Dog, Australian Cattle Dog, Australian Shepherd, Australian Terrier, Basenji, Basset Hound, Beagle, Bearded Collie, Beauceron, Bedlington Terrier, Belgian Malinois, Belgian Sheepdog, Belgian Tervuren, Bernese Mountain dog, Bichon Frise, Black and Tan Coonhound, Black Russian Terrier, Bloodhound, Bluetick Coonhound, Border Collie, Border Terrier, Borzoi, Boston Terrier, Bouview des Flandres, Boxer, Boykin Spaniel, Briard, Brittany, Brussels Griffon, Bull Terrier, Bulldog, Bullmastiff, Cairn Terrier, Canaan dog, Cane Corso, Cardigan Welsh Corgi, Cavalier King Charles Spaniel, Cesky Terrier, Chesapeake Bay Retriever, Chihuahua, Chinese Crested, Chinese Shar-Pei, Chow Chow, Cirneco dell'Etna, Clumber Spaniel, Cocker Spaniel, Collie, Curly-Coated Retriever, Dachshund, Dalmatian, Dandie Dinmont Terrier, Doberman Pinscher, Dogue de Bordeaux, English Cocker Spaniel, English Foxhound, English Setter, English Springer Spaniel, English Toy Spaniel, Entlebucher Mountain Dog, Field Spaniel, Finnish Lapphund, Finnish Spitz, Flat-Coated Retriever, French bulldog, German Pinscher, German Shepherd Dog, German Shorthaired Pointer, German Wirehaired Pointer, Giant Schnauzer, Glen of Imaal Terrier, Golden Retriever, Gordon Setter, Great Dane, Great Pyrenees, Greater Swiss Mountain Dog, Greyhound, Harrier, Havanese, Ibizian Hound Icelandic Sheepdog, Irish Red and White Setter, Irish Setter, Irish Terrier, Irish Water Spaniel, Irish Wolfhound, Italian Greyhound, Japanese Chin, Keeshond, Kerry Blue Terrier Komondor, Kuvasz, Labrador Retriever, Lakeland Terrier, Leonberger, Lhasa Apso, Lowchen, Maltese, Manchester Terrier, Mastiff, Miniature Bull Terrier, Miniature Pinscher, Miniature Schnauzer, Neapolitan Mastiff, Newfoundland, Norfolk Terrier, Norwegian Buhund, Norwegian Elkhound, Norwegian Lundehund, Norwich Terrier, Nova Scotia Duk Tolling Retriever, Old English Sheepdog, Otterhound, Papillion, Parson Russell Terrier, Pekingese, Pembroke Welsh Corgi, Petit Basser Griffon Vendeen, Pharaoh Hound, Plott, Pointer, Polish Lowland Sheepdog, Pomeranian, Poodle, Portuguese Water Dog, Pug, Puli, Pyrencan Shepherd, Rat Terrier, Redbone Coonhound, Rhodesian Ridgeback, Rottweiler, Russsell Terrier, Saint Bernard, Saluki, Samoyed, Schipperke, Scottish Deerhound, Scottish Terrier, Sealyham Terrier, Shetland Sheepdog, Shiba Inu, Shih Tzu, Siberian Husky, Silky Terrier, Skye Terrier Smooth Fox Terrier, Soft Coated Wheaten Terrier, Spinone Italiano, Staffordshire Bull Terrier, Standard Schnauzer, Sussex Spaniel, Swedish Vallhund, Tibetan Mastiff, Tibetan Spaniel, Tibetan Terrier, Toy Fox Terrier, Treeing Walker Coonhound, Vizsla, Weimaraner, Welsh Springer Spaniel, Welsh Terrier, West Highland White Terrier, Whippet, Wire Fox Terrier, Wirehaired Pointing Griffon, Xoloitzcuintli, and Yorkshire Terrier.

Flea and Tick Control Products

There are numerous flea and tick control products currently available for use in controlling fleas and ticks on felines. Products from the major manufacturers are sold as monthly topicals, most as "spot on" applications to the skin of the animal. All kill adult fleas and, although most purport to kill ticks; the majority do not kill flea eggs. Products containing fipronil will kill lice but none of those products claim to repel flies.

Most main line manufacturers of flea/tick products employ various concentrations of fipronil, dinotefuran, imidacloprid or etofenprox in combination with pyriproxyfen or (S) methoprene. Few botanicals appear to be effective except for a mixture of natural botanical oils sold by Sergeant's which is stated to be effective against adult fleas, ticks and lice comparable to products containing fipronil. Table 2 lists the active ingredients for some popular commercial products typically supplied as topical treatments.

SUMMARY OF THE INVENTION

The invention relates to new liquid formulations containing high concentrations of hydrophilic and hydrophobic insecticides, particularly relating to compositions comprising dinotefuran, etofenprox and pyriproxyfen as the active components. Dinotefuran is a neo-nicotinoid compound which is water soluble, while etofenprox is essentially insoluble in water. Other water soluble neo-nicotinoids such as nitenpyram could be used although most neo-nicotinoids are relatively insoluble in aprotic polar solvents and do not dissolve sufficiently to form a stable solution with the hydrophobic component. In most preferred formulations, the hydrophobic component is the ether pyrethrin etofenprox, which can be prepared in a weight percent range of 40-60% in an aprotic polar solvent with dinotefuran and pyriproxyfen. The weight percent of the solvent or mixed solvents is below 35%. The active hydrophilic and hydrophobic components form stable solutions with a shelf life of at least several months.

There are several solvents and combinations of solvents that may be employed to solubilize the mixture of hydrophilic and hydrophobic active ingredients in the disclosed liquid formulations. Such solvents include N-methyl pyrrolidone (NMP), propylene carbonate, ethyl acetate, tetrahydrofurfuryl alcohol (THFFA), glycofurol, glycerol formal, solketal (alone or in combination with DMSO), 4-hydroxy-1,3-dioxane, 1,2-glycerol-formal and N-octylpyrrolidone. A preferred solvent is N-octylpyrrolidone, which can be combined with NMP or propylene carbonate.

The invention provides a combination of active ingredients ("actives") particularly useful for topical treatment of not only ticks and fleas, but also flea eggs, flea larvae, ticks, tick eggs, tick nymphs, mites and mosquitoes in felines and canines.

A particularly surprising aspect of the disclosed formulation is the high concentration of hydrophilic and hydrophobic active substances which can be solubilized in aprotic polar liquids. Dinotefuran is hydrophilic and readily dissolves in water, while etofenprox is hydrophobic with essentially no solubility in water. Combinations of dinotefuran and etofenprox up to 40-60% by weight can be achieved in aprotic polar solvents. The liquid formulations containing high concentrations of an ether pyrethroid such as etofenprox are highly effective in controlling fleas and ticks and are nontoxic for use as topicals. Products that use permethrin rather than etofenprox cannot be used on felines due to toxicity. The disclosed formulations with high concentrations of etofenprox can be used effectively and safely on canines and felines, as well as other mammals such as rabbits, mice, rats and guinea pigs.

Topical solutions preferably comprise a mixture of dinotefuran, etofenprox and pyriproxyfen formulated in N-octylpyrrolidone or a mixture of N-octylpyrrolidone and NMP. Pyriproxyfen is an insect growth regulator that is present in 0.4-0.5 weight percent. In a typical preferred combination, dinotefuran is 4.95 weight percent, etofenprox is 60 weight percent, and pyriproxyfen is 0.44 weight percent in 34.6 weight percent N-octylpyrrolidone or a mixed solvent of 28.61 weight percent NMP and 6.00 weight percent N-octylpyrrolidone. This solution provides over 65 weight percent active ingredients and is effective as a spot-on formulation to control and kill fleas and ticks in cats and dogs.

DETAILED DESCRIPTION OF THE INVENTION

There are numerous products available for dogs, which act to kill or prevent fleas and ticks. A well-known spot topical treatment for dogs is a product containing fipronil, cyphenothrin and (S)-methoprene. The active ingredients in the composition for dogs 45-88 lbs. are in the range of about 22.8% by weight. The ingredients in Squeeze-On® for dogs are cyphenothrin and fipronil. This combination of actives is stated to kill fleas, flea eggs, flea larvae and ticks. These flea/tick formulations cannot be used on cats.

A typical flea treatment for cats is FRONTLINE® Feline, which is sold with only two active ingredients: fipronil and S-methoprene. The latter is an insect growth regulator. The active ingredients make up only about 12% while inert ingredients make up over 78% of the formulation. By comparison, the flea/tick formulations described here have much higher concentrations of active ingredients and are therefore more effective and long-lasting.

Table 3 exemplifies topical formulations illustrating the invention, preferably containing dinotefuran, pyriproxyfen and etofenprox. Dinotefuran is a member of the neo-nicotinoid class of insecticides and etofenprox is an ether pyrethroid. Most pyrethroids are esters. Pyriproxyfen is an insect growth regulator. Dinotefuran will kill fleas but not ticks; etofenprox will kill both fleas and ticks. Dinotefuran provides "speed of kill "that is not provided by etofenprox. Table 3 shows formulations containing dinotefuran, etofenprox and pyriproxyfen that can be applied as a topical "spot on" to animals. The formulations are particularly effective for use as topical applications on canines and felines to kill fleas, ticks and flea eggs.

Dinotefuran is a hydrophilic compound that will dissolve in water (approx. 40 g/L). Other neo-nicotinoids with a few exceptions are less soluble, as shown in Table 4. While dinotefuran is most preferred, nitenpyram is highly hydrophilic and could be used in formulations where higher levels of neo-nicotinoid would be desirable. The ether pyrethroid etofenprox will dissolve in some aprotic polar solvents to provide up to 40-60 weight percent while most ester pyrethroids had little solubility. Other ether pyrethroids may be useful provided they have insecticidal activity and may be desirable because of cost and relatively low hydrophobicity.

The described formulations are stable at temperatures from 0° F. up to at least 120° F. for one month at tested temperatures of 0°, 32°, 70° and 120° F. Table 5 shows the results of several formulations stored at temperatures ranging from freezing to 50° F. No precipitation or crystallization was observed.

Etofenprox is a hydrophobic compound that is relatively insoluble in water [1 mg/L]. Both dinotefuran and etofenprox are soluble in pyrrolidone compounds. N-octylpyrollidone is a preferred solvent that can be used either alone or mixed with other aprotic polar liquids. Other solvent systems are suitable and are listed in Table 2.

The new formulations are designed to be used on both canines and felines. Etofenprox is not toxic to felines, unlike other members of the pyrethroid class of insecticides. Most products available for dogs include pyrethoid esters which are toxic to felines and therefore cannot be used on cats. The formulations which have high levels of the ether pyrethroid etofenprox can be used on other mammals including rabbits, mice, rats, hamsters, and guinea pigs.

An important and unexpected aspect of the invention is the high concentration of total insecticide actives [approx. 45-65%] in solution that are stable at ambient and lower temperatures for extended periods of time. This is particularly unexpected because etofenprox is relatively insoluble in solvents that dissolve hydrophilic substances. The hydrophilic and hydrophobic actives in the described mixtures form stable solutions with good temperature stability. No precipitation or crystallization was observed in liquid formulations containing 40-60 weight percent etofenprox and up to 5% dinotefuran, although dinotefuran at 5% concentration may crystallize from many hydrophilic solvents at 0° F. and 32° F. Even with this high concentration of active ingredients, the solutions are stable for 1 month at tested temperatures of 0°, 32°, 70° and 120° F.

Flea Diseases

A lethal disease in cats is cytauxzoonosis, which is a blood parasite commonly found from central Kansas southward and eastward to about Jacksonville, Fla. There is no effective treatment for cytauxzoonosis.

The most common problem with fleas in both cats and dogs is flea allergy dermatitis. Fleas inject saliva into the skin when they are feeding causing the animal to itch where salivary protein is deposited at the site of the bite. Subsequent scratching can result in significant hair loss in the area of the bite.

Fleas can cause allergic reactions in both pets and humans. Flea bites on cats or dogs can result in hives or rashes which may promote a serious skin infection; for example, miliary dermatitis in cats. Humans are often bitten by fleas transferred from infested animals, resulting in itching, redness and varying degrees of dermatitis.

Anemia is an extremely serious condition which can result from fleas feeding on red blood cells in severe flea infestations. The condition is particularly serious in kittens and puppies where loss of red blood cells affects ability to efficiently carry oxygen to the brain. Even after treatment for anemia, the animals may have lasting brain damage.

Tape Worms are carried inside fleas and are transmitted to cats and dogs when the animals lick or chew on flea bites. The ingested tapeworm reproduces in the digestive system and can grow to several feet in length. Infected dogs or cats, particularly young ones, fail to thrive and are typically underweight.

Plague is a disease that affects humans even in modern times. The disease is transmitted to humans through flea bites, most frequently to pet owners in areas with flea infestations. Fleas typically are brought into homes by pets which may or may not show evidence of fleas.

Most common in the Southern states, murine typhus is carried by fleas, from both wild animals and pets such as cats or dogs. Typical symptoms of murine typhus include backache, abdominal pain, headache, nausea, vomiting, and a red rash. The worst symptom of this condition is the extremely high fever that it causes (of 105-106 degrees), which can last for weeks.

Tick Diseases in Pets

There are several diseases that can be transmitted to a pet from a tick bite. The most common tick-borne diseases seen in the United States are Lyme disease, Rocky Mountain spotted fever, ehrlichiosis, and tick paralysis. These and some of the other tick-borne diseases that particularly affect dogs and cats are listed below.

Also called borreliosis, Lyme disease is caused by the bacteria *Borrelia burgdorferi*. Deer ticks carry these bacteria, transmitting them to the animal while sucking its blood. The tick must be attached to the dog (or cat) for about 48 hours in order to transmit the bacteria to the animal's bloodstream. If the tick is removed within a day or two, transmission will usually not occur.

Common signs of Lyme disease include lameness, fever, swollen lymph nodes and joints, and reduced appetite. In severe cases, animals may develop kidney disease, heart conditions, or nervous system disorders. Animals do not develop the tell-tale "lyme disease rash" that is commonly seen in humans with Lyme disease.

Blood tests are necessary to diagnose Lyme disease in pets. Oral antibiotics are generally prescribed if the tests are positive. Dogs that have recovered from Lyme disease can get the disease again because no immunity is conferred. A vaccine for Lyme disease is available for dogs, but unfortunately, the vaccine is not available for cats.

A disease seen commonly in dogs in the east, Midwest, and plains region of the U.S. is Rocky Mountain spotted fever Cats can be infected with RMSF, but the incidence is much lower for them. The organisms that cause RMSF are transmitted by the American dog tick and the Rocky Mountain spotted fever tick.

The tick must be attached to the dog or cat for at least five hours in order for transmission of the organism to occur. Signs of RMSF may include fever, reduced appetite, depression, pain in the joints, lameness, vomiting, and diarrhea. Some animals may develop heart abnormalities, pneumonia, kidney failure, liver damage, or even neurological signs (e.g., seizures, stumbling).

Blood tests are used to detect antibodies to the organism. This indicates that at one time the animal has been infected. Oral antibiotics are used for about two weeks to treat the infection. Unlike Lyme Disease, animals that clear the organism usually recover and remain immune to future infection. If the dog or cat has heart, liver, or kidney damage, and/or the nervous system has been affected by the infection, it may require additional supportive treatment, generally in hospital.

Currently, there is no vaccine available to prevent RMSF, so tick control is important for animals living in endemic areas.

Ehrlichiosis is also a tick-borne disease affecting dogs. It is transmitted by the brown dog tick and the Lone Star Tick and is caused by a rickettsial organism. It occurs worldwide and is found in every state in the U.S. Common symptoms include depression, reduced appetite (anorexia), fever, stiff and painful joints, and bruising. Signs typically appear less than a month after a tick bite and last for about four weeks.

Special blood tests may be needed to test for antibodies to *Ehrlichia*. Antibiotics are usually given for up to four weeks to completely clear the organism. After infection, the animal may develop antibodies to the organism, but will not be immune to reinfection. There is no vaccine available for ehrlichiosis. Low doses of antibiotics may be recommended for animals during tick season in areas of the country that are endemic to this disease.

Deer ticks and western black-legged ticks carry the bacteria that transmit canine anaplasmosis. Another form of anaplasmosis caused by a different bacterium is carried by the brown dog tick. Both dogs and cats are at risk for this condition. Because the deer tick also carries other diseases, some animals may be at risk for developing more than one tick-borne disease at the same time.

Signs of anaplasmosis are similar to ehrlichiosis and include pain in the joints, fever, vomiting, diarrhea, and possible nervous system disorders. Pets will usually begin to show signs of disease within a couple weeks after infection. Diagnosis of anaplasmosis will usually require blood tests, urine tests, and sometimes other specialized lab tests.

Oral antibiotics are given for up to a month for treatment of anaplasmosis, depending on the severity of the infection. When treated promptly, most pets will recover completely. Immunity is not guaranteed after a bout of anaplasmosis, so pets may be reinfected if exposed again.

Tick paralysis is caused by a toxin secreted by ticks. The toxin affects the nervous system in mammals. Dogs affected become weak and limp, while cats are usually affected to a lesser extent. Signs begin about a week after an animal is first bitten by ticks. It typically begins with a weakness in the rear legs, eventually involving all four limbs, followed by difficulty breathing and swallowing. Death may result if the condition progresses further.

If ticks are found on the animal, removal usually results in a rapid recovery. Depending on the severity of the condition, supportive treatment (e.g., breathing assistance) may be needed for survival. An antitoxin is available, which can be given if the condition is discovered soon after infection.

Haemobartonellosis is a disease transmitted by both ticks and fleas. It is caused by an organism that targets red blood cells in the affected animal, leading to anemia and weakness. Both cats and dogs are affected. In cats, the condition is also known as feline infectious anemia. In dogs, the disease is usually not apparent unless the animal already has underlying issues.

Diagnosis of haemobartonellosis is by examining blood samples for the organism. Specialized lab tests are also available. Treatment with antibiotics must be continued for several weeks, and transfusions may be necessary for some animals.

Also known as rabbit fever, tularemia is caused by a bacteria carried by four varieties of ticks in North America. Fleas may also carry and transmit tularemia to dogs and cats. Cats are usually more affected by this condition than dogs. Symptoms in dogs are reduced appetite, depression, and a mild fever. Cats will exhibit high fever, swollen lymph nodes, nasal discharge, and possibly abscesses at the site of the tick bite. Younger animals are usually at higher risk of contracting tularemia.

Blood tests are generally used to look for antibodies to the bacteria that cause tularemia, the presence of which signifies exposure and probable infection. Antibiotics are given to treat this condition in positively identified animals. There is no preventive vaccine for this condition, so keeping cats indoors and using flea and tick control measures are important. Restricting your pet from hunting rodents, rabbits, and animals that carry the disease will also help protect your pet from acquiring the disease.

Protozoa, those tiny single celled animal-like organisms, are the parties to blame when dogs and cats are diagnosed with babesiosis. Ticks transmit the protozoan organism to animals, where it sets itself up in the red blood cells, causing anemia. Babesiosis is usually seen in the southern U.S., but is also found in the northeastern part of the country.

Signs of babesiosis in dogs are typically severe. They include pale gums, depression, dark-colored urine, fever, and swollen lymph nodes. In severe cases, the animal may collapse suddenly and go into shock. Blood and urine tests, as well as specialized diagnostic testing, are used to look for signs of the organism in the affected animal.

Dogs that survive the disease usually remain infected and future relapses may occur. There is no vaccine available for protection from babesiosis.

Cats are at risk for being infected with cytauxzoonosis. This parasitic disease is transmitted by ticks and is more commonly reported in the south central and southeast United States. Cats typically become very ill when infected because the parasite affects many parts of the body.

Cats may develop anemia, depression, high fever, difficulty breathing, and jaundice (i.e., yellowing of the skin) Treatment is often unsuccessful, and death occurs in as short as one week following infection.

Immediate and aggressive treatment with specialized drugs, intravenous fluids and supportive care are typically necessary. Cats that recover from cytauxzoonosis but may be carriers of the disease for life. There is no vaccine for this disease, so tick prevention is important.

Dogs in the south central and southeastern United States are at greater risk for contracting American canine hepatozoonosis (ACH). The Gulf Coast tick carries this particular disease. This tick-borne disease is caused by the actual ingestion of a nymphal or adult stage tick, rather than by transmission through attachment and biting of the skin by the tick. It is suspected that the ingestion takes place during self-grooming, or when the dog eats an infected animal.

Infection is severe and often fatal. Symptoms include high fever, stiffness and pain upon movement, weight loss, and complete loss of appetite. The muscles will begin to waste away, an outward symptom that will become most apparent around the dog's head. Discharge from the eyes is also very common.

Tests can be done to find the parasites in the dog's blood, discharge, or muscle tissue. Treatment with anti-parasitic drugs, along with anti-inflammatories and antibiotics, is necessary for some time after diagnosis. If the dog recovers, follow-up medication for several years may be necessary, as a relapse of this disease is possible.

The most common problem with fleas in both cats and dogs is flea allergy dermatitis. Fleas inject saliva into the skin when they are feeding causing the animal to itch where salivary protein is deposited at the site of the bite. Subsequent scratching can result in significant hair loss in the area of the bite.

Ticks cause several diseases in both cats and dogs but only dogs get Lyme disease. Cats can acquire anaplasmosis and tularemia. Apparently rare, ticks can infect cats with Rocky Mountain spotted fever.

EXAMPLES

The following examples are provided as illustrations of the invention and are in no way to be considered limiting.

Example 1

Flea/Tick Formulations

Exemplary Formulations (A) dinotefuran, 4.95 g and etofenprox, 60.0 g, is dissolved in 54.6 g of N-octylpyrrolidone. The solution can be stored at least for one month at ambient temperatures. Alternatively, a dry mixture of dinotefuran and etofenprox with a respective mass weight ratio of 0.0825 can be shipped separately from N-octylpyrrolidone for combining in amounts to provide a weight % ratio of up to 60% for etofenprox and 4.95% for dinotefuran.

(B) Dinotefuran 4.95 g, etofenprox, 40-60 g and pyriproxyfen, 0.44 g are dissolved in 34-48 g of N-methylpyrrolidone and 6-10 g of N-octylpyrrolidone selected to provide a solution with a weight percent range of 40-60% of etofenprox, 4.95% dinotefuran, 0.44% pyriproxyfen and 6-10% N-octylpyrrolidone. The solution is stable at ambient temperature for at least one month.

(C) Dinotefuran 4.95 g, etofenprox, 40-60 g. pyriproxyfen, 0.44 g and 0.2 g piperonyl butoxide are dissolved in 34-48 g of N-methylpyrrolidone and 6-10 g of N-octylpyrrolidone selected to provide a solution with a weight percent ratio of 40-60% of etofenprox, 4.95% dinotefuran, 0.44% pyriproxyfen, 0.2% piperonylbutoxide and 6-10% N-octylpyrrolidone. The solution is stable at ambient temperature for at least one month.

Example 2

Application of High Concentration Flea/Tick Formulations

The formulations of Example 1 (A-C) are prepared in an N-octylpyrrolidone/N-methylpyrrolidone solvent with a nominal 60-65% by weight concentration of dinotefuran, and etofenprox and, optionally, pyriproxyfen and piperonyl, each less than 0.5 weight %. Topical applications are made monthly to a dog or cat in dosage amounts from 0.5-8 ml, preferably from 1.2 ml up to 5.96 ml depending on the weight of the animal.

Example 3

Dosage Applications in Dogs

Typically, the formulations in example 1 are applied to canines on a weight basis. Table 6 shows a typical dosage for a topical formulation with 55% etofenprox mass weight percent. The product can be applied as a spot at the base of the neck between the shoulder blades or as a stripe starting at the base of the neck and finishing at the base of the tail.

Example 4

Dosage Applications in Cats

Cat weights, with the exception of kittens, do not show the same variation as do dog weights. A 40% by weight Etofenprox formulation prepared as in example 1 is applied at a dosage of 1.8 ml. The product can be applied as a spot at the base of the neck by the shoulder blades or as a stripe starting at the base of the neck and finishing at the base of the tail.

TABLE 1

Cat and Dog Populations

| Country | Number | |
| --- | --- | --- |
| | Cats | Dogs |
| United States | 76,430,000 | 75,800,000 |
| China | 53,100,000 | 27,400,000 |
| Russia | 12,700,000 | 15,000,000 |
| Brazil | 12,466,000 | 35,700,000 |
| France | 9,600,000 | 7,400,000 |
| Italy | 9,400,000 | — |
| UK | 7,700,000 | — |
| Ukraine | 7,350,000 | — |
| Japan | 7,300,000 | 12,000,000 |
| Germany | 7,100,000 | — |
| Philippines | — | 22,600,000 |
| India | — | 10,200,000 |
| Argentina | — | 9,200,000 |
| Romania | — | 9,200,000 |

TABLE 2

| Product Name | Active Ingredient | Percent | Application Frequency |
| --- | --- | --- | --- |
| FRONTLINE PLUS ® | Fibronil | 9.8% | Monthly |
| | (S)methoprene | 11/8% | |
| SENTRY ® | etofenprox | 55% | Monthly |
| | pyriproxyfen | 2.5% | |
| BIOSPOT ON FOR CATS ® | etofenprox | 40% | Monthly |
| | (S)methoprene | 3.6% | |

TABLE 3

| Ingredient | Lot # 12-06-90A %/w/w | Lot # 12-06-91B* %/w/w | Lot # 12-06-92C* %/w/w | Lot # 12-06-93D* %/w/w | Lot # 12-06-94E %/w/w | Lot # 12-06-95F %/w/w | Lot # 12-06-97H %/w/w | Lot # 12-06-98I %/w/w |
|---|---|---|---|---|---|---|---|---|
| Dinotefuran | 4.95 | 4.95 | 4.95 | 4.95 | 4.95 | 4.95 | 4.95 | 4.95 |
| Permethrin | 36.08 | | | | | | | |
| Etofenprox | 0.00 | 40.00 | 50.00 | 60.00 | 40.00 | 40.00 | 40.00 | 40.00 |
| Pyriproxyfen | 0.44 | 0.44 | 0.44 | 0.44 | 0.44 | 0.44 | 0.44 | 0.44 |
| NMP | 58.53 | 48.61 | 38.61 | 28.61 | 44.61 | 34.61 | 34.61 | 34.61 |
| N-octylpyrrolidone | 6.00 | 6.00 | 6.00 | 6.00 | 10.00 | 10.00 | 10.00 | 10.00 |
| Propylene carbonate | | | | | | 10.00 | | |
| THFFA | | | | | | | | 10.00 |
| Ethyl lactate | | | | | | | 10.00 | |
| | 100.00 | 100.00 | 100.00 | 100.00 | 100.00 | 100.00 | 100.00 | 100.00 |

TABLE 4

| Neo-Nicotinoids | Water Solubility (g/liter) |
|---|---|
| Acetamiprid | 2.95 |
| Clothianidin | 0.327 |
| Imidacloprid | 0.5 |
| Nitenpyram | 840 |
| Sulfoxaflor | 0.568 |
| Thiacloprid | 0.185 |
| Thiamethoxam | 4.1 |
| Dinotefuran | 39.83 |

Nitenpyram and dinotefuran have high water solubility and can be described as hydrophilic.

TABLE 6

| Weight | Dosage |
|---|---|
| 5-14 lbs. | 0.5 ml |
| 15-30 lbs. | 1.95 ml |
| 31-60 lbs. | 3.90 ml |
| 61-150 lbs. | 6.50 ml |

The invention claimed is:

1. A composition comprising a hydrophilic neo-nicotinoid ingredient and an ether pyrethroid ingredient dissolvable in an aprotic polar solvent to provide a solution comprising 55 to 65 weight percent of the ether pyrethroid.

TABLE 5

Ambient, Freezer and Refrigerator storage

| | Ingredient | Lot # 12-06-90A %/w/w | Lot # 12-06-91B %/w/w | Lot # 12-06-92C %/w/w | Lot # 12-06-93D %/w/w | Lot # 12-06-94E %/w/w | Lot # 12-06-95F %/w/w | Lot # 12-06-97H %/w/w | Lot # 12-06-98I %/w/w |
|---|---|---|---|---|---|---|---|---|---|
| 1 | Dinotefuran | 4.95 | 4.95 | 4.95 | 4.95 | 4.95 | 4.95 | 4.95 | 4.95 |
| 2 | Permethrin | 36.08 | | | | | | | |
| 3 | Etofenprox | 0.00 | 40.00 | 50.00 | 60.00 | 40.00 | 40.00 | 40.00 | 40.00 |
| 4 | Pyriproxyfen | 0.44 | 0.44 | 0.44 | 0.44 | 0.44 | 0.44 | 0.44 | 0.44 |
| 5 | NMP | 52.53 | 48.61 | 38.61 | 28.61 | 44.61 | 34.61 | 34.61 | 34.61 |
| 6 | N-octylpyrrolidone | 6.00 | 6.00 | 6.00 | 6.00 | 10.00 | 10.00 | 10.00 | 10.00 |
| 7 | Propylene carbonate | | | | | | 10.00 | | |
| 8 | THFFA | | | | | | | | 10.00 |
| 9 | ethyl lactate | | | | | | | 10.00 | |
| | | 100.00 | 100.00 | 100.00 | 100.00 | 100.00 | 100.00 | 100.00 | 100.00 |

Evaluation Feb. 20, 2013

| | | | | | | | | |
|---|---|---|---|---|---|---|---|---|
| Ambient Storage | | S | S | S | S | S | S | S |
| Freezer (Immediately) | | S | S | S | S | S | S | S |
| After Freeze/Thaw | | S | S | S | S | S | S | S |
| Refrigerator | | S | S | S | S | S | S | S |
| 50° C. storage | | S | S | S | S | S | S | S |

Evaluation Feb. 28, 2013

| | | | | | | | | |
|---|---|---|---|---|---|---|---|---|
| Ambient Storage | | S | S | S | S | S | S | S |
| Freezer (Immediately) | | S | S | S | S | S | S | S |
| After Freeze/Thaw | | S | S | S | S | S | S | S |
| Refrigerator | | S | S | S | S | S | S | S |
| 50° C. storage | | S | S | S | S | S | S | S |

Evaluation Mar. 8, 2013

| | | | | | | | | |
|---|---|---|---|---|---|---|---|---|
| Ambient Storage | | S | S | S | S | S | S | S |
| Freezer (Immediately) | | S | S | S | S | S | S | S |
| After Freeze/Thaw | | S | S | S | S | S | S | S |
| Refrigerator | | S | S | S | S | S | S | S |
| 50° C. storage | | S | S | S | S | S | S | S |

S = soluble, H = Hazy, P = precipitate

2. The composition of claim 1 further comprising an insect growth regulator.

3. The composition of claim 2 further comprising 0.1 to 0.3 weight percent of a synergist to enhance ether pyrethroid activity, said synergist selected from piperonyl butoxide and n-octyl bicycloheptene dicarboximide.

4. The composition of claim 1 wherein the ether pyrethroid ingredient and the hydrophilic ingredient are any of their pharmaceutically acceptable salts, enantiomers, racemates, prodrugs, derivatives or metabolites.

5. The composition of claim 1 wherein the hydrophilic neo-nicotinoid is nitenpyram or dinotefuran.

6. The composition of claim 1 wherein the ether pyrethroid is etofenprox or silafluofen.

7. The composition of claim 2 wherein the insect growth regulator is pyriproxyfen, methoprene, or fenoxycarb.

8. The composition of claim 2 wherein the weight percent of the hydrophilic neo-nicotinoid, ether pyrethroid and the insect growth regulator comprises 55 to 65 weight percent in an aprotic polar solvent.

9. The composition of claim 1 wherein the aprotic polar solvent is selected from one or more of N-octylpyrrolidone, N-methylpyrrolidone, tetrahydrofurfuryl alcohol, propylene carbonate, and ethyl acetate.

10. The composition of claim 1 wherein the weight percent of etofenprox is 60 weight percent.

11. The composition of claim 5 wherein the weight percent of dinotefuran is 4 to 6 weight percent.

12. The composition of claim 7 wherein the weight percent of pyriproxyfen is 0.3 to 0.5 weight percent.

13. A method for topical treatment of fleas and ticks in a fur bearing animal comprising topically administering an effective amount of the composition of claim 8.

14. The method of claim 13 wherein a small volume is topically administered to cats or dogs.

15. The method of claim 14 wherein the volume is 1 to 8 ml.

16. The method of claim 15 wherein the volume is administered periodically each 30 to 60 days.

17. A kit for treating fleas and ticks in animals, comprising a solution of 55 to 65 weight percent of etofenprox, 4 to 5 weight percent of dinotefuran and optionally 0.3 to 0.5 weight percent pyriproxyfen in an aprotic polar solvent selected from N-methylpyrrolidone, N-octylpyrollidone, propylene carbonate, tetrahydrofurfuryl alcohol, ethyl lactate or mixtures thereof.

18. The kit of claim 17 further comprising 0.3 to 0.5 weight percent pyriproxyfen.

19. The kit of claim 18 further comprising 0.1 to 0.2 weight percent piperonyl butoxide or n-octyl bicycloheptene dicarboximide.

20. The kit of claim 17 comprising individually packaged solution volumes selected from 0.5 to 8 ml for spot treating cats or dogs.

* * * * *

UNITED STATES PATENT AND TRADEMARK OFFICE
CERTIFICATE OF CORRECTION

Page 1 of 1

PATENT NO. : 8,853,282 B1
APPLICATION NO. : 14/284658
DATED : October 7, 2014
INVENTOR(S) : Ian Cottrell It is certified that error appears in the above-identified patent and that said Letters Patent is hereby corrected as shown below:

In the Specification

Column 2,
Line 47, "afghan hound," should read --Afghan Hound,--.

Column 3,
Line 10, "Terrier Komondor," should read --Terrier, Komondor,--.
Lines 25-26, "Terrier Smooth" should read --Terrier, Smooth--.

Column 8,
Line 49, "skin) Treatment" should read --skin). Treatment--.

Signed and Sealed this
Fourteenth Day of July, 2015

Michelle K. Lee
*Director of the United States Patent and Trademark Office*